US009442083B2

(12) United States Patent
Turner et al.

(10) Patent No.: US 9,442,083 B2
(45) Date of Patent: Sep. 13, 2016

(54) 3D BACKSCATTER IMAGING SYSTEM

(75) Inventors: D. Clark Turner, Payson, UT (US); Ross Whitaker, Salt Lake City, UT (US)

(73) Assignee: Aribex, Inc., Orem, UT (US)

( * ) Notice: Subject to any disclaimer, the term of this patent is extended or adjusted under 35 U.S.C. 154(b) by 0 days.

(21) Appl. No.: 13/396,388

(22) Filed: Feb. 14, 2012

(65) Prior Publication Data

US 2013/0206985 A1 Aug. 15, 2013

(51) Int. Cl.
*G01N 23/20* (2006.01)
*G01N 23/203* (2006.01)
*G01N 23/10* (2006.01)

(52) U.S. Cl.
CPC ............ *G01N 23/203* (2013.01); *G01N 23/10* (2013.01); *G01N 23/20008* (2013.01); *G01N 23/20066* (2013.01); *G01N 2223/053* (2013.01); *G01N 2223/063* (2013.01)

(58) Field of Classification Search
CPC ........... G01N 23/20; G01N 23/20008; G01N 23/20015; G01N 23/20025; G01N 23/20075; G01N 23/20091; G01N 23/201; G01N 23/203; G01N 23/207; G01N 23/10; G01N 23/20016; G01N 23/20066; G01N 2223/053; G01N 2223/063; G01V 5/005; G01V 5/0025
USPC .............. 250/306, 307, 310, 311; 378/86–89
See application file for complete search history.

(56) References Cited

U.S. PATENT DOCUMENTS 4,825,454 A 4/1989 Annis et al.
5,729,582 A * 3/1998 Ham et al. ...................... 378/89
6,282,260 B1 8/2001 Grodzins
6,735,279 B1 5/2004 Jacobs et al.
7,130,374 B1 10/2006 Jacobs et al.

(Continued)

FOREIGN PATENT DOCUMENTS

CN 200941097 8/2007
WO 2004068915 8/2004

(Continued)

OTHER PUBLICATIONS

Backscatter (Wikipedia entry), http://en.wikipedia.org/wiki/backscatter.*

(Continued)

*Primary Examiner* — Robert Kim
*Assistant Examiner* — David E Smith
(74) *Attorney, Agent, or Firm* — Kenneth E. Horton; Kirton McConkie

(57) ABSTRACT

Systems and methods for imaging an object using backscattered radiation are described. The imaging system comprises both a radiation source for irradiating an object that is rotationally movable about the object, and a detector for detecting backscattered radiation from the object that can be disposed on substantially the same side of the object as the source and which can be rotationally movable about the object. The detector can be separated into multiple detector segments with each segment having a single line of sight projection through the object and so detects radiation along that line of sight. Thus, each detector segment can isolate the desired component of the backscattered radiation. By moving independently of each other about the object, the source and detector can collect multiple images of the object at different angles of rotation and generate a three dimensional reconstruction of the object. Other embodiments are described.

27 Claims, 3 Drawing Sheets

(56) References Cited

U.S. PATENT DOCUMENTS

| | | | |
|---|---|---|---|
| 7,162,005 | B2 | 1/2007 | Bjorkholm |
| 7,203,276 | B2 * | 4/2007 | Arsenault ........ G01N 23/20008 378/57 |
| 7,224,772 | B2 | 5/2007 | Jacobs et al. |
| 7,231,017 | B2 | 6/2007 | Gertsenshteyn et al. |
| 7,508,910 | B2 | 3/2009 | Safai et al. |
| 7,620,150 | B1 * | 11/2009 | Annis ............................ 378/87 |
| 2004/0068169 | A1 | 4/2004 | Mansfield et al. |
| 2005/0031078 | A1 * | 2/2005 | Kumakhov .......... G01N 23/223 378/87 |
| 2006/0062351 | A1 * | 3/2006 | Yokhin et al. .................. 378/86 |
| 2006/0065836 | A1 * | 3/2006 | Tsuchiya et al. .......... 250/363.1 |
| 2006/0140343 | A1 * | 6/2006 | Gibson et al. .................. 378/71 |
| 2008/0219403 | A1 * | 9/2008 | Moore .............................. 378/9 |
| 2009/0161818 | A1 * | 6/2009 | Sakurai ................ A61B 6/4291 378/15 |
| 2011/0096901 | A1 | 4/2011 | Kotowski et al. |
| 2011/0200164 | A1 * | 8/2011 | Blaj .................................. 378/4 |
| 2011/0200172 | A1 * | 8/2011 | Shedlock et al. ............... 378/87 |
| 2012/0087462 | A1 * | 4/2012 | Ikhlef ............................... 378/4 |

FOREIGN PATENT DOCUMENTS

| | | |
|---|---|---|
| WO | 2006122244 | 11/2006 |
| WO | 2009129488 A1 | 10/2009 |

OTHER PUBLICATIONS

Meng, Christopher Lloyd; Computed Image Backscatter Radiography: Proof of Principle and Initial Development, University of Florida (2008).

European Patent Office, Search Report for EP13155279, Aug. 13, 2013.

* cited by examiner

3D BACKSCATTER IMAGING SYSTEM

This invention was made with Government support under contact NNX10CF73P awarded by NASA. The Government has certain rights in this invention.

FIELD

This application relates generally to systems for creating images. More particularly, this application relates to imaging systems that use radiography to detect scatter field components (including backscattering) and methods of using imaging systems.

BACKGROUND

In many industrial, military, security or medical applications, images of an internal structure of objects are required. Radiography is one type of technique that can be used for imaging. Radiography generally comprises either conventional transmission radiography or backscatter radiography. When access behind an object to be interrogated is not possible, only backscatter radiography is possible. One method of backscatter imaging is Compton Backscatter Imaging (CBI), which is based on Compton scattering.

Lateral migration radiography (LMR) is one type of imaging based on CBI that utilizes both multiple-scatter and single-scatter photons. LMR uses two pairs of detector with each pair having a detector that is uncollimated to predominantly image single-scatter photons and the other detector collimated to image predominantly multiple-scattered photons. This allows generation of two separate images, one containing primarily surface features and the other containing primarily subsurface features.

Recently, backscatter radiography by selective detection (RSD), a variant of LMR, has been used. RSD uses a combination of single-scatter and multiple-scatter photons from a projected area below a collimation plane to generate an image. As a result, the image has a combination of first-scatter and multiple-scatter components, offering an improved subsurface resolution of the image.

SUMMARY

This application relates to imaging systems that use radiography to detect scatter field components (including backscattering) and methods of using such imaging systems. The imaging system comprises a radiation source for irradiating an object, the radiation source movable about the object. The imaging system also contains a detector for detecting backscattered radiation from the object. The detector can be disposed on substantially the same side of the object as the source and the detector can be rotationally movable about the object. The radiation source and the detector can move independently of each other about the object, including in a rotational movement, collecting multiple images of the object at different angles of rotation. These multiple images can be used to generate a three dimensional reconstruction of the object.

The radiation source can comprise x-ray, gamma ray, neutron, an electron beam source, or combinations thereof. The beam of the radiation source can be a pencil beam, fan beam, cone beam, or a combination thereof. The detector may comprise a photostimuable phosphorous-based image plate, TFT-based flat panel detector, an amorphous silicon panel, a digitizing field screen, or a combination thereof. The detector (or detectors) can be separated into multiple detector segments (i.e., using a collimator grid) so that each segment has a single line of sight projection through the object and so only detects radiation along that line of sight. The restricted line of sight allows each detector segment to isolate the desired component of the backscattered radiation.

The imaging system can be used for single-sided, non-destructive imaging of any desired object in many different industries, including medical, military, security, and other industries. The imaging system can analyze a wide variety of objects, such as buried or otherwise unobservable objects suspected of containing a bomb (e.g. landmine), voids or imperfections in a material, luggage, cargo, integrated circuits, or other items.

The imaging system images the object using radiation from the source. When radiation is backscattered towards the detector, it can be received through the collimator grid and isolated to each detector segment. Each detector segment has a "field of view" of small area on the object of interest. By processing the data collected by each detector segment, an image of the object can be generated. The source and/or the detector can then be moved or rotated to a different orientation about the object, radiation is again directed to the object, and backscattered radiation is again detected by each detector segment. By processing the data again collected by the detector segment, another image of the object can be generated. To further enhance the image, the source and/or the detector can be moved multiple times to gather data from multiple orientations (i.e., up to 360°). The multiple data sets may also be used for reconstructing the data into a three-dimensional image.

BRIEF DESCRIPTION OF THE DRAWINGS

The following description can be better understood in light of the Figures, in which.

Figure 1:
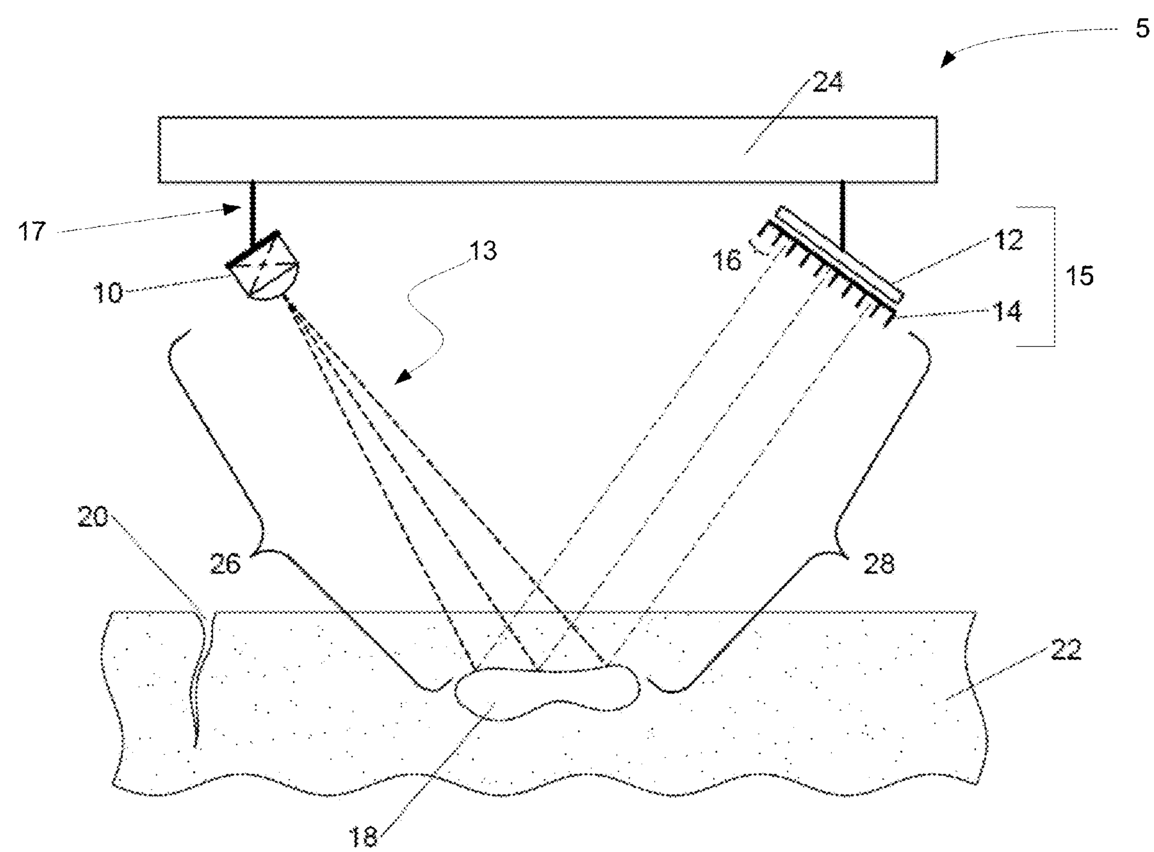
FIG. 1 illustrates some embodiments of an imaging system using radiography to detect backscattering.

The Figures illustrate specific aspects of the imaging systems and methods for using the imaging systems. Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices. Moreover, the Figures may show simplified or partial views, and the dimensions of elements in the Figures may be exaggerated or otherwise not in proportion for clarity.

DETAILED DESCRIPTION

The following description supplies specific details in order to provide a thorough understanding. Nevertheless, the skilled artisan will understand that the described imaging system and associated methods of making and using the system can be implemented and used without employing these specific details. Indeed, the imaging system and associated methods can be placed into practice by modifying the described systems and methods and can be used in conjunction with any other apparatus and techniques conventionally used in the industry. For example, while the description below focuses on using the imaging system for x-rays, it could be used for other types of radiations, such as gamma rays, neutrons, electron beams, or combinations thereof.

As the terms on, attached to, or coupled to are used herein, one object (e.g., a material, a layer, a substrate, etc.) can be on, attached to, or coupled to another object regardless of whether the one object is directly on, attached, or coupled to the other object or there are one or more intervening objects between the one object and the other object. Also, directions (e.g., above, below, top, bottom, side, up, down, under, over, upper, lower, horizontal, vertical, “x,” “y,” “z,” etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements.

Some embodiments of the imaging systems and methods for using the imaging systems are shown in the Figures. FIG. 1 illustrates one imaging system which can be used for detecting backscattered radiation. As used herein, backscatter includes any scattering radiation occurring away from the surface of the irradiated object or material.

The system 5 contains a source of radiation 10. The radiation source (or source) 10 can be any source (or sources) of radiation that penetrates the desired object (or objects), including an x-ray source, a gamma ray source, a neutron source, an electron beam source, or combinations thereof. The source 10 irradiates the desired object area (including the object itself) using the desired type of radiation to a desired depth.

In some embodiments, the amount of radiation (or intensity) from the source 10 can be controlled and customized for a specific object. For example, the radiation source 10 can be controlled to provide a photon illumination (energy) spectrum with an average depth in the object to obtain the detail need to create an image. In another example, the radiation intensity provided by radiation source 10 can be sufficiently low so as to not saturate the detector 12 (described below).

As shown in FIG. 1, the radiation source 10 transmits radiation 26 which partially or completely penetrates the surface of a material 22 that is part of an object or object area to be analyzed. The radiation 26 strikes internal portions of the material 22, such as cracks 20, voids 18, or hidden objects in the material 22. Those internal portions in the material 22 then backscatter a portion of the radiation 26 as backscattered radiation 28. In some configurations, the radiation source 10 is also capable of independent motion in different directions including rotation, in-and-out movement of the radiation source 10 from the object region, and angular movement. The radiation source 10 can be adjusted to select or focus on the object that is being analyzed or scanner by the beam 13 of radiation 26. Alternatively, the radiation source can be stationary and the object can be movable.

The beam 13 from the radiation source 10 can be configured to be any type of known beam. In some configurations, the beam can be configured as a pencil beam, fan beam, cone beam, or combinations thereof. In some instances, a fan beam or cone beam can be used since they can create a higher intensity backscatter field and have a larger field of view than a pencil beam, thereby saving time due to the simultaneous collection from a larger field of view. The width and/or length of the fan and/or cone beam can be adjusted to enhance the resolution of the image.

Where a fan beam is used, it can be configured by utilizing an aperture. In these embodiments, the beam of radiation can be passed through the aperture such that the output from the aperture is a fan beam of radiation. These embodiments can increase the analysis speed by radiating a line of the object, instead of only a spot radiated by a pencil beam, and by using the fan beam to create a higher intensity backscatter field.

The system 5 also contains a detector 12. The detector 12 can be any detector (or detectors) of radiation that can detect the radiation scattered from the object. In some embodiments, the detector can include an x-ray detector, a gamma ray detector, a neutron detector, an electron beam detector, or combinations thereof. In other embodiments, the detector 12 can comprise NaI scintillator crystals, plastic scintillators, photostimuable phosphorous-based image plates, TFT-based flat panel detectors, amorphous silicon panels, or combinations thereof. For example, for x-ray radiography on a large area image, a photostimuable phosphor-based imaging plate and/or an amorphous silicon panel (ASP) conversion screen bonded to an array of photosensitive diodes.

The detector(s) can be separated into multiple detector segments that each detects radiation along a single path or line of sight. This separation can be accomplished using any mechanism that isolates each segment so that it only receives radiation along that path. For example, in the embodiments depicted in FIG. 1, the detector 12 comprises a collimator 14 coupled to the detector 12 and so is referred to as a collimated detector 15. The collimator contains multiple detector segments within each grid of the collimator. In the embodiments depicted in FIG. 1, the radiation source 10 and the collimated detector 15 can be disposed on the same side of the object region to be analyzed. The radiation source 10 can generate photons that are directed toward the object region. The collimated detector 15 collects photons that are backscattered from the surfaces of the object and from objects hidden or voids beneath the surfaces. The collimated detector not only detects the backscattered radiation, but also assists in generating three-dimensional images of the object area, including hidden objects and/or voids.

The collimator 14 can include any of a variety of cross sectional areas, including a cylindrical, elliptical (non-circular), or rectangular. In some embodiments, the collimator 14 and the detector 12 have the shape so that any or all of the backscattered radiation that travels through the collimator 14 is detected. The collimator 14 may include any number of collimator features with various geometries including fins, slates, screens, and/or plates that may be curvilinear or flat. In some embodiments, the collimator 14 (and such features) can be formed from any known radiation absorbing material, such as lead. In other embodiments, the collimator 14 (and such features) can be formed from radiation reflective material, such as high density plastic, aluminum, or combinations thereof. These latter embodiments are helpful when enhancement, rather than removal, of certain backscatter radiation is desired. In some configurations, the collimator features can be oriented substantially perpendicular to the surface of the detector 12. In other configurations, the collimator features can be given any orientation relative to the detector 12 that provides the desired line of sight radiation for each segment.

In some configurations, the separation of the detector using the collimator can create apertures 16. Backscattered radiation from the object reaches the detector 12 through the apertures 16 if the backscatter direction is substantially parallel to the collimator features or has a narrow enough angle to travel through the aperture without being absorbed by the collimator feature. The collimator features can be modified to allow for a wider aperture to allow in more backscattered radiation or a narrower aperture to decrease the backscattered radiation from the object.

In some embodiments, the collimator 14 may be adjustable to alter the direction of the backscattered radiation which can reach the detector. In these embodiments, the position and/or orientation of the collimator features can be modified to change the position and/or orientation by manual mechanisms or by automatic mechanisms, such as through computer controlled motor drives.

The collimator 14 can be coupled to the detector using any known technique. In some embodiments, the collimator 14 can be optically coupled to the detector 12 so that radiation passing by the collimator 14 reaches the detector 12 and is measured, creating a collimated detector 15. In other embodiments, the collimator 14 can be physically attached to the detector 12.

The collimated detector 15 can move in different directions including rotation, in-and-out movement from the object region, and angular movement. In some configurations, the collimator 14 can move in different directions relative to the detector, including rotation, in-and-out movement, and angular movement. These movements can focus the image by selecting and/or isolating the desired backscattered radiation. In other words, adjusting the collimated detector 15 allows the user to select and isolate particular vectors of backscattered radiation to travel through the aperture 16 and be detected by the detector 12. Alternatively, the collimated detector can be stationary and the object movable.

In some embodiments, the radiation source 10 and the collimated detector 15 may be attached to a moving structure (such as plate 24), as shown in FIG. 1. The plate 24 has a movement axis that is substantially perpendicular to the object. In some embodiments, this movement axis is a rotational axis and so the plate 24 is a rotational plate. (Such rotational axis is shown as axis 35 in FIG. 2*a*.) The radiation source 10 and collimated detector 15 may be attached to the plate 24 as known in the art, such as poles 17 extending from the rotating plate 24. The radiation source 10 and collimated detector 15 may be located at any location along the plate 24 and this location can be fixed or altered as desired. This configuration allows both the collimated detector 15 to detect backscatter and the source 10 to irradiate the object from any location along the plate 24.

In these embodiments, the rotational axis of the plate 24 allows the source 10 and collimated detector 15 to be rotated about the object region while maintaining a similar distance and orientation from the object. Independent adjustments can be made to the source 10 and collimated detector 15 to change the distance and orientation from the object, if needed. In some configurations, the plate 24 may comprise a single plate so the source 10 and the collimated detector 15 remain at about an 180° angle relative each other. In other configurations, the plate 24 may be two plates, attached or separate, to allow the radiation source 10 and collimated detector 15 to be rotated independently and oriented at any desired angle relative to each other. For example, the radiation source 10 may remain in a fixed position while the collimated detector 15 can be rotated to create various angles of orientation relative to the source 10.

In some embodiments, the system 5 can be contained in a protective and supportive housing which can be made from any known flexible and/or known lightweight materials. The housing holds the various components of the system 5 in place. Lightweight housing materials facilitate portability of the system, which can be advantageous in certain applications. Using such materials also allows the housing to be manufactured in a variety of desired shapes and allows the system to be relatively lightweight to make it easy to transport. In some embodiments, the system 5 can be configured as a compact system so that it is readily transportable and adopted to work within confined spaces.

Figure 2B:
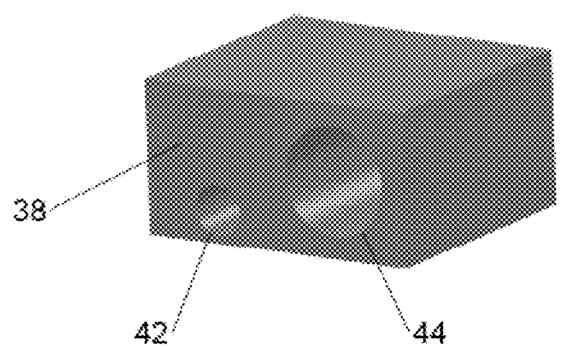
FIG. 2*b* comprises a three-dimensional image obtained by using a reconstruction method on the images obtained in FIG. 2*a*.
Figure 2A:
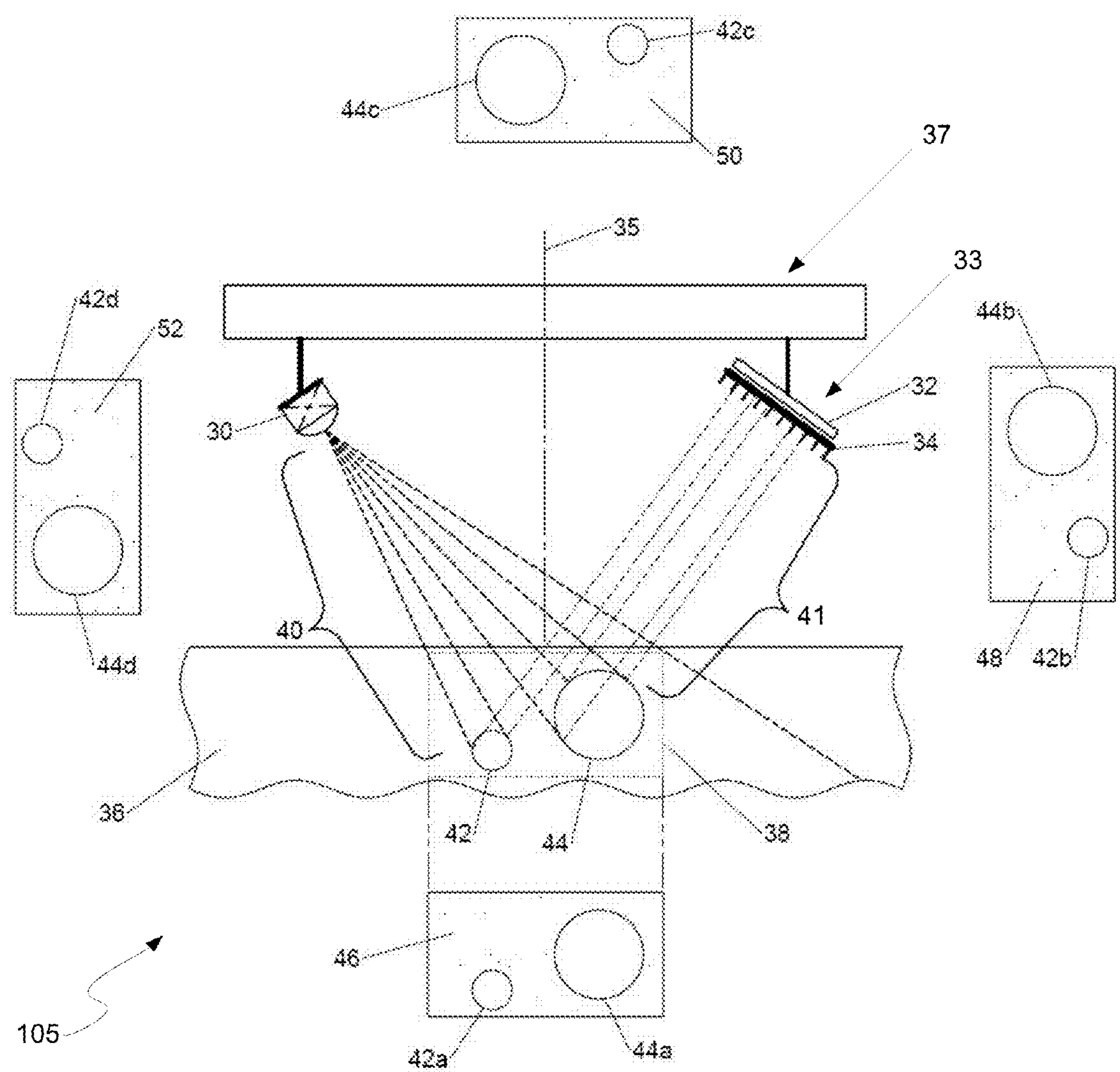
FIG. 2*a* depicts other embodiments of the imaging system and the images obtained from the system.

In some embodiments, the system 105 can be used to detect backscattered radiation, as shown in FIG. 2*a*. In this Figure, a radiation source 30 transmits radiation 40 which penetrates the surface of a material 36 and strikes internal details such as voids 42 and 44, hidden objects, and/or cracks (not shown) in the material 36. These internal details in the material 36 then backscatter a portion of the transmitted radiation 41. The backscatter 41 can pass through a collimator 34 and be detected by the detector 32.

In these embodiments, the radiation source 30 can generate photons that are directed toward an object (including object region 38) and the collimated detector 33 collects photons that are backscattered from the scanned surface and from the internal details beneath the scanned surface. The object region 38 can be shifted by independent adjustments to the radiation source 30 or by changing the location of the radiation source 30 along a rotating plate 37. For example, adjustments can be made to the object region 38 by changing the distance from the radiation source 30 to the object region 38, which will shrink or enlarge amount of the object region 38 being irradiated. Further, the object region 38 can be shifted by changing the angle of the radiation source 30 with respect to the object region 38.

In these embodiments, the beam from the radiation source 30 may be a pencil beam, a fan beam, or a cone beam. With a cone beam it is possible to scan the entire object region 38 without the need to move or modify the radiation source 30. The cone beam may also be moved to increase or decrease the size of the object region. When using a pencil beam or fan beam, it can scan a specific part of the object region 38. The imaging system 105 can use any scanning design, including raster scanning, to create a desired object region 38. The object region 38 can be a variety of cross sectional areas, including cylindrical, elliptical (non-circular), or rectangular (includes square). As explained in further detail below, data gathered from multiple orientations of the radiation source 30 and collimated detector 33 should be of approximately the same object region 38.

The configuration of the radiation source 30 and the collimated detector 33 allow the acquisition of multiple sets of data or images from the object region 38. Therefore, it is possible to obtain multiple images of the same object region 38 from different orientations between the radiation source 30 and the collimated detector 33. In some embodiments, the orientation between the source 30 and the collimated detector 33 can range from about 1° up to about 359° relative to each other. For example, an image of an object region 38 may be collected when the radiation source 30 and the collimated detector 33 are initially at a 180° angle with respect to each other, and thereafter the radiation source 30 can be rotated in 10° increments around the object region 38, collecting an image at each location. The subsequent application of a computer model on these multiple images will allow a three-dimensional reconstruction of the object region 38.

As shown in FIG. 2*a*, multiple images 46, 48, 50, and 52 can be taken from various configurations of the radiation source 30 and the collimated detector 33. Although FIG. 2*a* depicts four images, any number of images could be used to obtain a three-dimensional reconstruction. In some embodiments, the number of images can range from 2 (with appropriate constraints) to any desired number. In other embodiments, the number of images can range from 3 or 4 to 10 or 15. Of course, the more images that are taken, the better the resolution of the 3D reconstruction.

Image 46 can be obtained by data collected from the configuration of the source 30 and collimated detector 33 depicted in FIG. 2*a*. The voids 42 and 44 found in the material 36 can be depicted in image 46 as two-dimensional objects 42*a* and 44*a*. Image 48 can be obtained by rotating the radiation source 30 and/or the collimated detector 33 by the desired amount and collecting additional data to depict the voids 42 and 44 as two-dimensional objects 42*b* and 44*b*. To obtain image 48, the radiation source 30 and collimated detector 33 were both rotated 90° about the object region 38 in the same direction (e.g. remaining at a 180° angle with respect to each other). Image 50 can be obtained by rotating both the radiation source 30 and collimated detector 33 another 90° about the object region 38 in the same direction depicting the voids 42 and 44 as two-dimensional objects 42*c* and 44*c*. In some configurations, the configuration used to generate image 50 could be the mirror image of the configuration shown in FIG. 2*a*, having the radiation source 30 located on the right side of the system and the collimated detector located on the left side of the system. Image 52 is obtained by again rotating the radiation source 30 and collimated detector 33 another 90° about the object region 38 in the same direction depicting the voids 42 and 44 as two-dimensional objects 42*d* and 44*d*.

Rotation about the object region 38 can be accomplished by rotating plate 37 around rotational axis 35 that is oriented substantially perpendicular to the material 36. In these embodiments, the plate 37 may be a single plate that rotates the radiation source 30 and collimated detector 33 at the same rotational distance from each other (i.e. the radiation source 30 and collimated detector 33 remain 180° from each other). In other embodiments, the plate 37 may be two plates, attached or separate, that allow the radiation source 30 and collimated detector 33 to rotate at different rotational distances with respect to each other. Rotation about the object region can also be accomplished by keeping the radiation source 30 and collimated detector 33 stationary and rotating the object region 38.

FIG. 2*b* depicts a three-dimensional (3D) structure of the object region 38 and voids 42 and 44 using the images 46, 48, 50, and 52. This 3D structure can be obtained using the reconstruction method described herein. The reconstruction method can be used to supply a three-dimensional structure of any desired feature of the material 36, including voids, cracks, corrosion, delaminations, or other hidden objects.

The mathematical formulation, which gives rise to a forward or generative model, for use in reconstruction is as follows. The formulation only considers photons returning to the detector from a single backscatter rather than multiple scattering events. The collimated detector establishes a set of apertures each of which has an associated line of sight. Incident photons move along the associated line of sight, which is a three-dimensional space defined by the location and orientation of the aperture.

Figure 3:
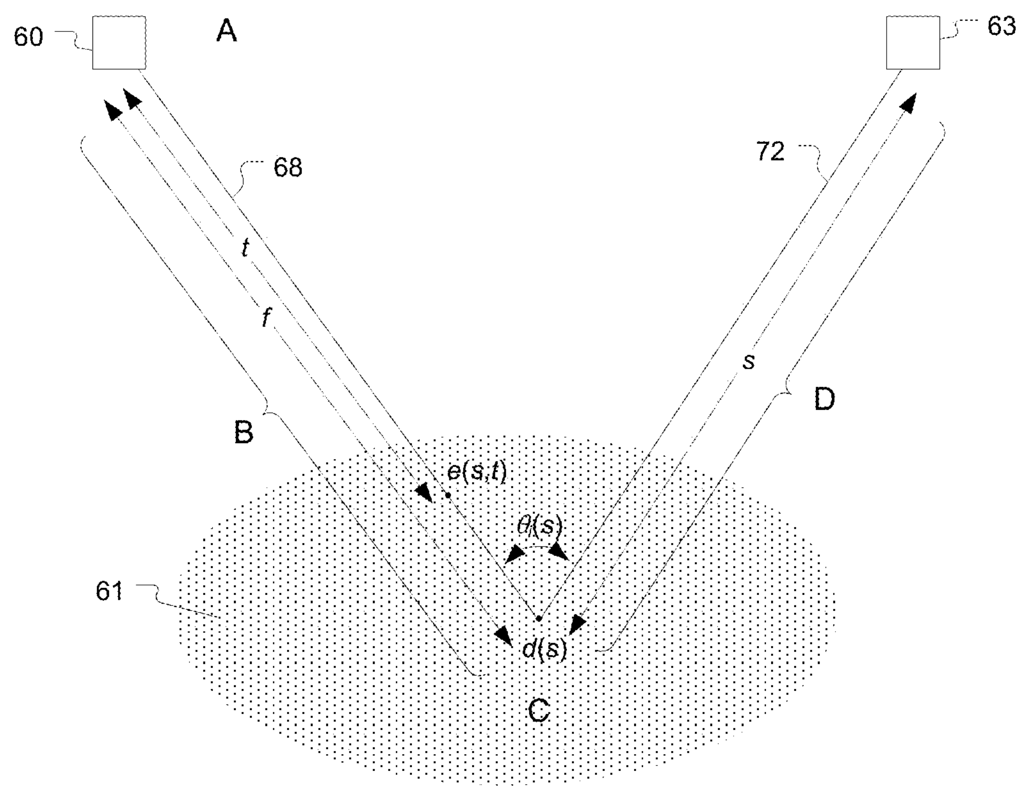
FIG. 3 illustrates some embodiments of simulation details that can be used in the reconstruction method.

FIG. 3 shows the simulation details for an embodiment of the reconstruction method. The region of space 61 to be imaged is called the object region. The position along collimated line 72 a distance s from the detector segment 63 is referred to as d(s). Line 68 connects d(s) with source 60. The position along the line 68 a distance t from the radiation source is referred to as e(s,t). The distance from d(s) to the radiation source 60 is referred to as f.

The expression for the number of photons, or signal intensity, reaching the detector segment 63 from backscatter at d(s) can include four terms: (A) the number of photons radiated from the radiation source 60, (B) the loss of intensity traveling along line 68 from the radiation source 60 as it passes through a material in the object region to reach d(s), (C) the fraction of that intensity that is scattered along line 72, and (D) the loss of intensity as the backscattered photons travel along line 72 to the detector. The cumulative effects of terms A, B, C, and D are multiplicative and thus the mathematical expression for the intensity reaching the detector along a single path i, from a backscatter at a distance s is:

$$E_i(s)=A\times B\times C\times D=E_0 e^{-\int_0^f \rho(e_i(t,s))dt}\gamma(\theta_i(s))\rho(d_i(s))\, e^{-\int_s^o \rho(d_i(q))dq}; \tag{1}$$

where $E_0$ is the intensity of the radiation source 60, ρ(x) is the material density as a function of the position x in the object region, $\theta_i(s)$ is the angle formed by the two lines 68 and 72, and $\gamma(\theta_i(s))$ is the differential scattering cross section as a function of the angle at which the two lines meet. In order to model the effects of Compton scattering $\gamma(\theta_i(s))$ can be set equal to $\cos^2(\theta)$. Alternatively, other models of the scattering can be used and substituted into equation (1).

The total intensity traveling along path i is the integral of all the backscatter events along the line 72. This is:

$$E_i=\int_0^\infty E_i(s)ds=E_0\int_0^\infty e^{-\int_0^f \rho(e_i(t,s))dt}\gamma(\theta_i(s))\rho(d_i(s))\, e^{-\int_s^0 \rho(d_i(q))dq}ds, \tag{2}$$

where, in practice, the integral along d(s) ends at the effective boundaries of the object region (i.e. no material or signal becomes insignificant).

The basic form of equations 1 and 2, unlike conventional tomography or tomosynthesis, does not lend itself to an easy decomposition into linear expressions of ρ, the image density. Rather there is a nonlinear mixture of terms—a combination of the multiplicative effect of the backscattering term with the exponential terms that model the intensity loss and the composition of backscattering along the line of sight, represented as the outermost integral in Equation 2.

For reconstruction the term $A=E_0$ can be treated as a constant and absorbed into the detector units. The constant can be estimated globally or measured separately before imaging. The form for Equation 2 in terms of the integral along the detector segment line of sight and the image density therefore becomes:

$$\frac{E_i}{E_0}=\int_0^\infty B_i(\rho,s)C_i(s)\rho(d_i(s))D_i(\rho,s)ds, \tag{3}$$

where the functions $B_i$ and $D_i$ are nonlinear functions of ρ. By treating the nonlinear interactions as secondary and using a fixed estimate for ρ, denoted as $\bar{\rho}$, the equation becomes:

$$M_i=\frac{E_i}{E_0}=\int_0^\infty B_i(\rho,s)C_i(s)\rho(d_i(s))D_i(\rho,s)ds=\int_0^\infty w_i(s)\rho(d_i(s)), \tag{4}$$

where the terms that do not depend explicitly on ρ into $w_i(s)$ are combined. The result is a linear operator, and thus, an expression for the image formulation that is of the same form as a conventional x-ray formation—and, by analogy, tomographic reconstruction.

Considering the discrete form of Equation 4, the approximation of ρ on a grid or individual detector segment is denoted as $R_k$, the value of ρ at a grid location is denoted as $X_k$, and the number of projection images collected as N. The discrete reconstruction $R_k$ is designed to optimize the total difference between the measured detector intensities and those simulated from applying the imaging model to the discrete reconstruction, $R_k$. As shown in equation (4), the function $w_i(s)$ can be captured as a set of weights $W_{ij}$ that measures the relationship between the fixed estimated $\bar{\vec{\beta}}$, the solution on the grid $R_k$ where the backscatter occurs, and the corresponding line integrals from the radiation source 60 and detector segment 63 to the point. Then the reconstruction is formulated as:

$$R = \text{argmax}_R \sum_{j=1}^{N} \left( \sum_{i=1}^{M} W_{ij} R_j - M_i \right)^2, \tag{5}$$

where, M is the number of grid points (e.g., detector segments) in the reconstruction, and R represents the entire collection of grid points in the solution. R represents the object that is to be reconstructed and M represents the projection data collected. The weights $W_{ij}$ can be computed in a manner that is similar to conventional computer tomography, that is, by using a linear interpolation (e.g. trilinear in 3D) and using the geometric relationships between the grid and the line integral to establish this linear dependence for each pair of points on the detector and the reconstruction grid.

The least squares problem in Equation 5 can be solved as an over-constrained linear system. The linear system in Equation 5 can be solved in a variety of ways including standard numerical relaxation (linear system) methods and conventional iterative methods such as the algebraic reconstruction technique (ART) or simultaneous algebraic reconstruction technique (SART). If SART is used, the algorithm formulates the reconstruction problem as finding an array of unknown variables using algebraic equations from the projection data. It is an iterative reconstruction algorithm, which has the advantage of robustness to noise and incomplete projection data. As the ART and SART algorithms, and variations thereof, are known to one of skill in the art, they will not be described further.

Due to the nature of the formulation and underlying physics $\bar{\vec{\beta}}$ can be treated as fixed. Because the integrals in Equation (4) average (or smooth) the effects of the material properties between source-detector and position of the backscatter, and thus, aggregate material properties along the rays is sufficient to obtain some level of accuracy in the reconstruction.

The accuracy results depend on the accuracy of the models of the intensity loss that takes places as radiation moves to and from the point of backscatter. Iterative reconstruction can be used, denoting as a sequence of solutions $R^0, R^1, R^2, \ldots$, and a sequence of discrete estimates of the solution used to model intensity loss $\hat{R}^0, \hat{R}^1, \hat{R}^2, \ldots$. This gives a sequence of weights in the linear system, $W^l_{ij}$. In implementation, the estimates of $\bar{\vec{R}}^j$ simply lag in the formulation. In this way $\bar{\vec{R}}^{j\,l} = R^{l-1}$ and $W^l$ can be computed from the intensity loss estimated from the previous solution and they change with each subsequent iteration. Such schemes can be effective for nonlinear optimization problem (i.e., let the nonlinear terms lag).

Some embodiments pertain to a method and apparatus for a single-sided, non-destructive imaging technique utilizing the penetrating power of radiation to image subsurface and surface features. These embodiments can be used for a variety of applications including non-destructive examination, medical imaging, military, and security purposes.

Figure 4:
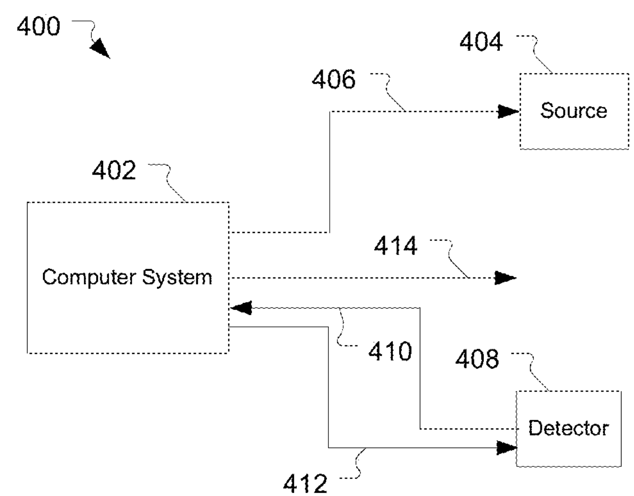
FIG. 4 illustrates a block diagram backscatter imaging system in accordance with some embodiments of the invention.

Implementation of the reconstruction algorithms can be conveniently performed using various means for reconstruction. In some embodiments, a conventional processing system (such as, for example, a computer) can provide a means for reconstruction using computer tomography. In particular, the algorithms can be implemented in software for execution on one or more general purpose or specialized processor(s). The software can be compiled or interpreted to produce machine executable instructions that are executed by the processor(s). The processor can accept as inputs any of the following:

a. Orientation/position of the object relative to the source
b. Orientation/position of the object relative to the detector
c. Output signal (array of signals) from the detector If desired, the processor can also control the relative positioning of the object relative to the source and detector. Thus, the processor can output any of the following:

a. Rotational control for the object
b. Linear positioning control for the source
c. Linear positioning control for the detector FIG. 4 illustrates an example of a system for backscatter imaging. The system 400 can include a computer subsystem 402 (which can, for example, be a personal computer, workstation, web server, or the like). The computer system can be of conventional design, including a processor, memory (data storage and program storage), and input/output. The computer system can include a display (e.g., for displaying reconstructed images) and human input devices (e.g., keyboard, mouse, tablet, etc.). The computer system can interface to a radiation source 404, to and provide control information 406 to the radiation source. For example, control information can provide for turning on/off the radiation output of the source and setting the source output intensity. The system can include mechanical means (e.g., as described above) for moving the source, in which case the control information can also control the position/orientation of the source.

The system 400 can also include a detector 408 which can provide measurements 410 of detected backscattered radiation to the computer system 402. For example, the measurements can be digital data provided from the detector. As another example, the measurements can be analog data, and can be converted (e.g., using an analog to digital converter) into digital form before processing. The system can include mechanical means (e.g., as described above) for moving the detector, in which case control information 412 can be provided from the computer system to the detector to control the position/orientation of the detector.

The computer system 402 can be programmed to implement reconstruction techniques (e.g., as described above) to combine data from multiple two-dimensional slices of detected backscattered radiation 410 to form a three-dimensional reconstructed image. The three-dimensional reconstructed image can be output for display, stored in a memory for later use, or transmitted via a communications link (e.g., the Internet) to another location for display or storage.

If desired, the system 400 can also include means for moving the object to be imaged (e.g., as described above) in which case the computer system 402 can provide control output 414 for controlling the position/orientation of the object.

Applications of embodiments of the present invention include, but are not limited to scanner/imaging systems for detecting flaws and defects in materials and structures, scanners for detecting target objects and/or foreign object debris inside of walls and structures, devices for security purposes to identify objects hidden in walls, containers or on individuals, portal scanning, law enforcement and other security applications, and medical imaging.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. An apparatus for imaging an object, comprising:

a radiation source configured to irradiate an object with a fan or cone beam, the radiation source movable relative to the object; and a detector configured to detect backscattered radiation from within the object at a depth sufficient to create a two dimensional image, the detector having a substantially two-dimensional area, wherein the detector is disposed on substantially the same side of the object as the source, the detector divided into segments, each segment configured to detect a single radiation path from the object;

wherein the radiation source and the detector are arranged to have a first angle between them and are configured to rotate about an axis between them while maintaining the first angle at a substantially constant value to collect multiple images of the object at different angles of rotation about the axis.

2. The apparatus of claim 1, wherein the detector comprises a collimator configured to divide the detector into detector segments.

3. The apparatus of claim 1, wherein the radiation source comprises an x-ray source, a gamma ray source, a neutron source, an electron beam source, or a combination thereof.

4. The apparatus of claim 1, wherein the beam comprises a cone beam.

5. The apparatus of claim 1, further comprising a rotating plate having a rotational axis substantially perpendicular to the object, the radiation source and the detector being mounted to the rotating plate.

6. The apparatus of claim 1, wherein the radiation source has an adjustable orientation angle with respect to the object.

7. The apparatus of claim 1, wherein the detector has an adjustable orientation angle with respect to the object.

8. The apparatus of claim 1, wherein the radiation source and the detector have an adjustable distance with respect to the object.

9. The apparatus of claim 2, wherein the collimator comprises a grid configured to restrict the backscattered radiation impinging on each detector segment.

10. An apparatus for imaging an object, comprising:

a radiation source configured to irradiate an object with a fan or cone beam, the radiation source rotationally movable about the object;

a detector configured to detect backscattered radiation from within the object at a depth sufficient to create a two dimensional image, the detector having a substantially two-dimensional area, wherein the detector is disposed on substantially the same side of the object as the source, wherein the detector is rotationally movable about the object and the detector is divided into segments, each segment configured to detect a single radiation path from the object, and wherein the radiation source and the detector are arranged to have a first angle between them and are configured to rotate about a central axis between them while maintaining the first angle at a substantially constant value to collect multiple images of the object at different angles of rotation about the axis; and a processor coupled to the detector and configured to accept measurements of the backscattered radiation and construct a three-dimensional image of the object from the measurements;

wherein the object, the radiation source, the detector, or a combination thereof are movable relative to each other.

11. The apparatus of claim 10, wherein the detector comprises a collimator configured to divide the detector into detector segments.

12. The apparatus of claim 10, wherein the radiation source comprises an x-ray source, a gamma ray source, a neutron source, an electron beam source, or a combination thereof.

13. The apparatus of claim 10, further comprising a rotating plate having a rotational axis substantially perpendicular to the object, the radiation source and the detector being mounted to the rotating plate.

14. The apparatus of claim 10, wherein the radiation source and the detector have an adjustable orientation angle with respect to the object.

15. The apparatus of claim 11, wherein the collimator comprises a grid configured to restrict the backscattered radiation impinging on each detector segment.

16. The apparatus of claim 10, wherein the beam comprises a cone beam.

17. An apparatus for imaging of an object, comprising:

means for irradiating the object with a radiation fan or cone beam means for detecting backscattered radiation from within the object at a depth sufficient to create an image, the detecting means having a substantially two-dimensional area, the detecting means being positioned on a same side of the object as the irradiating means and the detecting means being divided into segments, each segment configured to detect a single radiation path from the object, wherein the irradiating means and the detecting means are arranged to have a first angle between them and are configured to rotate about a central axis between them while maintaining the first angle at a substantially constant value to collect multiple images of the object at different angles of rotation about the axis;

means for moving the object relative to each of the irradiating means and the detecting means; and means for reconstructing a three-dimensional image of the object from the detected backscattered radiation obtained at a plurality of positions of the object relative to the irradiating means and the detecting means.

18. The apparatus of claim 17, wherein the radiation beam comprises a cone beam.

19. A method of imaging an object, comprising:

providing a detector divided into segments that each detect a single radiation path from the object, the detector having a substantially two-dimensional area;

using a radiation source to irradiate an object with a first fan or cone beam of radiation, wherein the object emits first backscattered radiation;

receiving the first backscattered radiation through a collimator and detecting the first backscattered radiation using the detector segments;

rotating the radiation source and the detector about a central axis between them while maintaining a substantially constant angle between the radiation source and the detector;

irradiating the object with a second fan or cone beam of radiation, wherein the object emits second backscattered radiation;

receiving the second backscattered radiation through the collimator and detecting the second backscattered radiation using the detector segments; and forming a three-dimensional image of the object using the detected first backscattered radiation and the detected second backscattered radiation.

20. The method of claim 19, further comprising:

repeating the rotating;

irradiating the object region with additional beams of penetrating radiation, wherein the object emits additional backscattered radiation;

receiving the additional backscattered radiation and detecting the additional backscattered radiation using the detector segments; and wherein forming the image comprises using the additional backscattered radiation.

21. The method of claim 19, wherein the forming the image comprises:

defining a three-dimensional grid of data points that correspond to part or all of the object to be reconstructed;

estimating reconstructed object characteristics at each data point within the grid based on the backscattered radiation;

calculating a predicted backscattered radiation based on the reconstructed object characteristics;

determining a difference between the predicted backscattered radiation and the detected backscattered radiation; and iteratively improving the reconstructed object characteristics based on that difference.

22. The method of claim 20, further comprising collecting multiple images of the object at different rotation angles to generate a three dimensional reconstruction of the object.

23. The method of claim 19, further comprising using a collimator grid to separate the detector into segments and restrict the backscattered radiation impinging on each detector segment.

24. The method of claim 19, wherein the radiation source and detector move on an axis that is substantially parallel to the object's longest axis.

25. The method of claim 19, wherein the detector detects backscattered radiation from within the object.

26. The method of claim 25, wherein the radiation is backscattered from within the object at a depth sufficient to create an image.

27. The method of claim 19, wherein each of the first and second beams comprises a cone beam.

* * * * *